United States Patent
Virtanen

(10) Patent No.: US 10,806,933 B2
(45) Date of Patent: Oct. 20, 2020

(54) PATIENT MONITORING SYSTEMS AND METHODS THAT DETECT INTERFERENCE WITH PACEMAKER

(71) Applicant: General Electric Company, Schenectady, NY (US)

(72) Inventor: Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 279 days.

(21) Appl. No.: 15/696,781

(22) Filed: Sep. 6, 2017

(65) Prior Publication Data

US 2019/0070419 A1  Mar. 7, 2019

(51) Int. Cl.
*A61B 5/0205* (2006.01)
*A61N 1/37* (2006.01)
(Continued)

(52) U.S. Cl.
CPC .......... *A61N 1/3704* (2013.01); *A61B 5/0205* (2013.01); *A61B 5/0809* (2013.01);
(Continued)

(58) Field of Classification Search
None
See application file for complete search history.

(56) References Cited

U.S. PATENT DOCUMENTS

| 5,368,026 A | 11/1994 | Swedlow et al. |
| 5,743,263 A | 4/1998 | Baker, Jr. |

(Continued)

FOREIGN PATENT DOCUMENTS

| EP | 2470068 A2 | 7/2012 |
| EP | 2432380 A4 | 3/2013 |

(Continued)

OTHER PUBLICATIONS

Pending U.S. Appl. No. 14/586,393, filed Dec. 30, 2014, entitled Common Display Unit for a Plurality of Cableless Medical Sensors:, Muuranto et al.

(Continued)

*Primary Examiner* — Erica S Lee
(74) *Attorney, Agent, or Firm* — Andrus Intellectual Property Law, LLP

(57) ABSTRACT

A patient monitoring system includes a heart rate monitor that monitors the physiological parameter from a patient and provides a heart rate indicator based on the physiological parameter, an impedance respiration monitor that measures impedance of the patient's chest and provides a respiration rate, a processor, and an interference detection module. The interference detection module is executable to determine a baseline heart rate while the impedance respiration monitor is not active. The impedance respiration monitor is then activated to measure impedance of the patient's chest to provide the respiration rate. Upon activating the impedance respiration monitor, the interference detection module is executable to assess the heart rate indicator for an interference check period and detect a threshold change in the heart indicator compared to the baseline heart rate during the interference check period. Upon detecting the threshold change, an interference alert is generated to notify a clinician regarding interference with a pacemaker on the patient.

20 Claims, 6 Drawing Sheets

(51) Int. Cl.

| | | |
|---|---|---|
| *A61B 5/08* | (2006.01) | |
| *A61N 1/365* | (2006.01) | |
| *A61N 1/372* | (2006.01) | |
| *A61B 5/00* | (2006.01) | |
| *A61B 5/0464* | (2006.01) | |
| *A61B 5/145* | (2006.01) | |
| *A61B 5/0245* | (2006.01) | |
| *A61B 5/11* | (2006.01) | |

(52) U.S. Cl.
CPC ......... *A61B 5/0816* (2013.01); *A61B 5/7217* (2013.01); *A61N 1/36521* (2013.01); *A61N 1/36578* (2013.01); *A61N 1/37258* (2013.01); *A61B 5/0245* (2013.01); *A61B 5/0464* (2013.01); *A61B 5/1118* (2013.01); *A61B 5/14542* (2013.01); *A61B 5/7246* (2013.01); *A61B 5/746* (2013.01)

(56) References Cited

U.S. PATENT DOCUMENTS

| | | |
|---|---|---|
| 5,830,135 A | 11/1998 | Bosque et al. |
| 6,005,658 A | 12/1999 | Kaluza et al. |
| 6,178,343 B1 | 1/2001 | Bindszus et al. |
| 6,594,511 B2 | 7/2003 | Stone et al. |
| 7,803,120 B2 | 9/2010 | Banet et al. |
| 7,993,275 B2 | 8/2011 | Banet et al. |
| 8,180,440 B2 | 5/2012 | McCombie et al. |
| 8,200,321 B2 | 6/2012 | McCombie et al. |
| 8,239,010 B2 | 8/2012 | Banet et al. |
| 8,321,004 B2 | 11/2012 | Moon et al. |
| 8,359,080 B2 | 1/2013 | Diab et al. |
| 8,364,226 B2 | 1/2013 | Diab et al. |
| 8,364,250 B2 | 1/2013 | Moon et al. |
| 8,419,649 B2 | 4/2013 | Banet et al. |
| 8,437,824 B2 | 5/2013 | Moon et al. |
| 8,442,607 B2 | 5/2013 | Banet et al. |
| 8,449,469 B2 | 5/2013 | Banet et al. |
| 8,475,370 B2 | 7/2013 | McCombie et al. |
| 8,506,480 B2 | 8/2013 | Banet et al. |
| 8,527,038 B2 | 9/2013 | Moon et al. |
| 8,545,417 B2 | 10/2013 | Banet et al. |
| 8,554,297 B2 | 10/2013 | Moon et al. |
| 8,570,167 B2 | 10/2013 | Al-Ali |
| 8,571,893 B2 | 10/2013 | Dashefsky et al. |
| 8,574,161 B2 | 11/2013 | Banet et al. |
| 8,591,411 B2 | 11/2013 | Banet et al. |
| 8,594,776 B2 | 11/2013 | McCombie et al. |
| 8,602,997 B2 | 12/2013 | Banet et al. |
| 8,622,922 B2 | 1/2014 | Banet et al. |
| 8,672,854 B2 | 3/2014 | McCombie et al. |
| 8,721,542 B2 | 5/2014 | Al-Ali et al. |
| 8,727,977 B2 | 5/2014 | Banet et al. |
| 8,738,118 B2 | 5/2014 | Moon et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,808,188 B2 | 8/2014 | Banet et al. |
| 8,847,740 B2 | 9/2014 | Kiani et al. |
| 8,852,094 B2 | 10/2014 | Al-Ali et al. |
| 8,888,700 B2 | 11/2014 | Banet et al. |
| 8,909,330 B2 | 12/2014 | McCombie et al. |
| 8,956,293 B2 | 2/2015 | McCombie et al. |
| 8,956,294 B2 | 2/2015 | McCombie et al. |
| 8,979,765 B2 | 3/2015 | Banet et al. |
| 8,989,853 B2 | 3/2015 | Zong |
| 9,055,928 B2 | 6/2015 | McCombie et al. |
| 9,095,316 B2 | 8/2015 | Welch et al. |
| 9,149,192 B2 | 10/2015 | Banet et al. |
| 9,161,700 B2 | 10/2015 | Banet et al. |
| 9,173,593 B2 | 11/2015 | Banet et al. |
| 9,173,594 B2 | 11/2015 | Banet et al. |
| 9,215,986 B2 | 12/2015 | Banet et al. |
| 2005/0101873 A1 | 5/2005 | Misczynski et al. |
| 2007/0167850 A1 | 7/2007 | Russell et al. |
| 2008/0300471 A1 | 12/2008 | Al-Ali et al. |
| 2009/0171167 A1 | 7/2009 | Baker, Jr. |
| 2009/0275807 A1 | 11/2009 | Sitzman et al. |
| 2010/0063367 A1 | 3/2010 | Friedman et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2011/0080294 A1 | 4/2011 | Tanishima et al. |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0288421 A1 | 11/2011 | Banet et al. |
| 2012/0029300 A1 | 2/2012 | Paquet |
| 2012/0108983 A1 | 5/2012 | Banet et al. |
| 2012/0190949 A1 | 7/2012 | McCombie et al. |
| 2012/0290033 A1* | 11/2012 | Cho .................. A61N 1/056 607/20 |
| 2013/0109937 A1 | 5/2013 | Banet et al. |
| 2013/0116515 A1 | 5/2013 | Banet et al. |
| 2014/0025010 A1 | 1/2014 | Stroup et al. |
| 2014/0081099 A1 | 3/2014 | Banet et al. |
| 2014/0088385 A1 | 3/2014 | Moon et al. |
| 2014/0142445 A1 | 5/2014 | Banet et al. |
| 2014/0163393 A1 | 6/2014 | McCombie et al. |
| 2014/0200415 A1 | 7/2014 | McCombie et al. |
| 2014/0235964 A1 | 8/2014 | Banet et al. |
| 2014/0257056 A1 | 9/2014 | Moon et al. |
| 2014/0275818 A1 | 9/2014 | Kassem et al. |
| 2014/0276145 A1 | 9/2014 | Banet et al. |
| 2014/0276175 A1 | 9/2014 | Banet et al. |
| 2014/0301893 A1 | 10/2014 | Stroup et al. |
| 2015/0042466 A1 | 2/2015 | Kiani et al. |
| 2015/0164437 A1 | 6/2015 | McCombie et al. |
| 2015/0196257 A1 | 7/2015 | Yousefi et al. |
| 2015/0208966 A1 | 7/2015 | Al-Ali |
| 2015/0282717 A1 | 10/2015 | McCombie et al. |
| 2019/0076048 A1* | 3/2019 | Takala .................. A61B 5/053 |

FOREIGN PATENT DOCUMENTS

| | | |
|---|---|---|
| EP | 2162059 A4 | 10/2013 |
| EP | 2470067 A4 | 10/2013 |
| EP | 2560550 A4 | 12/2013 |
| EP | 2675346 A1 | 12/2013 |
| EP | 2675348 A1 | 12/2013 |
| EP | 2775917 A2 | 9/2014 |
| EP | 2432378 A4 | 12/2014 |
| EP | 24442709 A4 | 12/2014 |
| EP | 2519144 A4 | 3/2015 |
| EP | 2658440 A4 | 4/2015 |
| EP | 2544584 A4 | 7/2015 |
| EP | 2910182 A2 | 8/2015 |
| WO | 2008154643 A1 | 12/2008 |
| WO | 2010135516 A2 | 11/2010 |
| WO | 2010148205 A1 | 12/2010 |
| WO | 2011032132 A2 | 3/2011 |
| WO | 2011032132 A3 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |
| WO | 2010135518 A1 | 11/2011 |
| WO | 2012077113 A2 | 6/2012 |

(56) References Cited

FOREIGN PATENT DOCUMENTS

| WO | 2012092303 A1 | 7/2012 |
| WO | 2012112885 A1 | 8/2012 |
| WO | 2012112891 A1 | 8/2012 |
| WO | 2013071014 A2 | 5/2013 |
| WO | 2013071014 A3 | 5/2013 |
| WO | 2014015254 A1 | 1/2014 |
| WO | 2014165620 A1 | 10/2014 |
| WO | 2015120330 A1 | 8/2015 |
| WO | 2015173539 A1 | 11/2015 |

OTHER PUBLICATIONS

Chew et al., 1997, "Inappropriate Rate Change in Minute Ventilation Rate Responsive Pacemakers Due to Interference by Cardiac Monitors," PACE, vol. 20, p. 276-282.

Lau et al., 2006, "Pacemaker Tachycardia in a Minute Ventilation Rate-Adaptive Pacemaker Inducted by Electrocardiographic Monitoring", The Authors, vol. 29, p. 438-440.

\* cited by examiner

PATIENT MONITORING SYSTEMS AND METHODS THAT DETECT INTERFERENCE WITH PACEMAKER

BACKGROUND

The present disclosure relates generally to medical devices and, more specifically, to medical monitoring devices, such as for monitoring a patient's respiration, and for detecting and/or avoiding interference by a patient monitor with a patient's pacemaker.

In the field of medicine, physicians often desire to monitor multiple physiological characteristics of their patients. Oftentimes, patient monitoring involves the use of several separate monitoring devices simultaneously, such as a respiration monitor, a pulse oximeter, a blood pressure monitor, a heart monitor, a temperature monitor, etc. These may be separate monitoring devices, which may be separately or jointly controlled by a central control unit, or may be multiple patient monitoring functions incorporated into a single multi-parameter monitor.

A problem has been recognized by professionals in the healthcare and patient monitoring fields where certain monitoring devices, especially monitoring devices relying on impedance measurements of the patient's chest, interfere with minute ventilation rate-adaptive pacemakers and induce pacemaker tachycardia. Minute ventilation rate-adaptive pacemakers (hereinafter, "MV controlled pacemakers") adjust heart rate based on the patient's respiration rate, i.e., minute volume. These devices determine the respiration rate using bio-impedance measurements that are very similar to those used by patient monitoring devices. If the carrier frequencies or the harmonic components of the frequencies of the bio-impedance measurements by the pacemaker and a patient monitor happen to coincide, the MV controlled pacemaker can miss measure the respiration rate and improperly adjust the heart rate. For example, the pacemaker may make an erroneous bio-impedance measurements due to such interference, leading to an improper heart rate change, often to the upper limit programmed for the device. This forces the patient's heart into a tachycardic rhythm. If the underlying interference is not understood by clinicians, the tachycardic rhythm may be (and has been) mistakenly interpreted by clinicians as ventricular tachycardia and can lead to the administration of improper medical treatments. Such issues are well documented in relevant literature, including at: Chew, E. W., et al., Inappropriate Rate Change in Minute Ventilation Rate Responsive Pacemakers Due to Interference by Cardiac Monitors, PACE 1997; 20[Pt. I]:276-28, and at Lau, W., et al., Pacemaker Tachycardia in a Minute Ventilation Rate-Adaptive Pacemaker Induced by Electrocardiographic Monitoring, PACE 2006; 29:438-440.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment of a method of controlling an impedance respiration monitor to monitor respiration of a patient includes monitoring a heart rate indicator from the heart rate monitor for at least a predefined stability period to determine a baseline heart rate for the patient when the impedance respiration monitor is not active to measure impedance of the patient's chest. The impedance respiration monitor is then activated to measure impedance of the patient's chest and provide a respiration rate. Upon activating the impedance respiration monitor, the heart rate indicator is monitored for an interference check period, including comparing the heart rate indictor to the baseline heart rate and detecting a threshold change in the heart rate indicator during the interference check period. Once the threshold change is detected, an interference alert is generated to notify a clinician regarding interference with a pacemaker on the patient.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
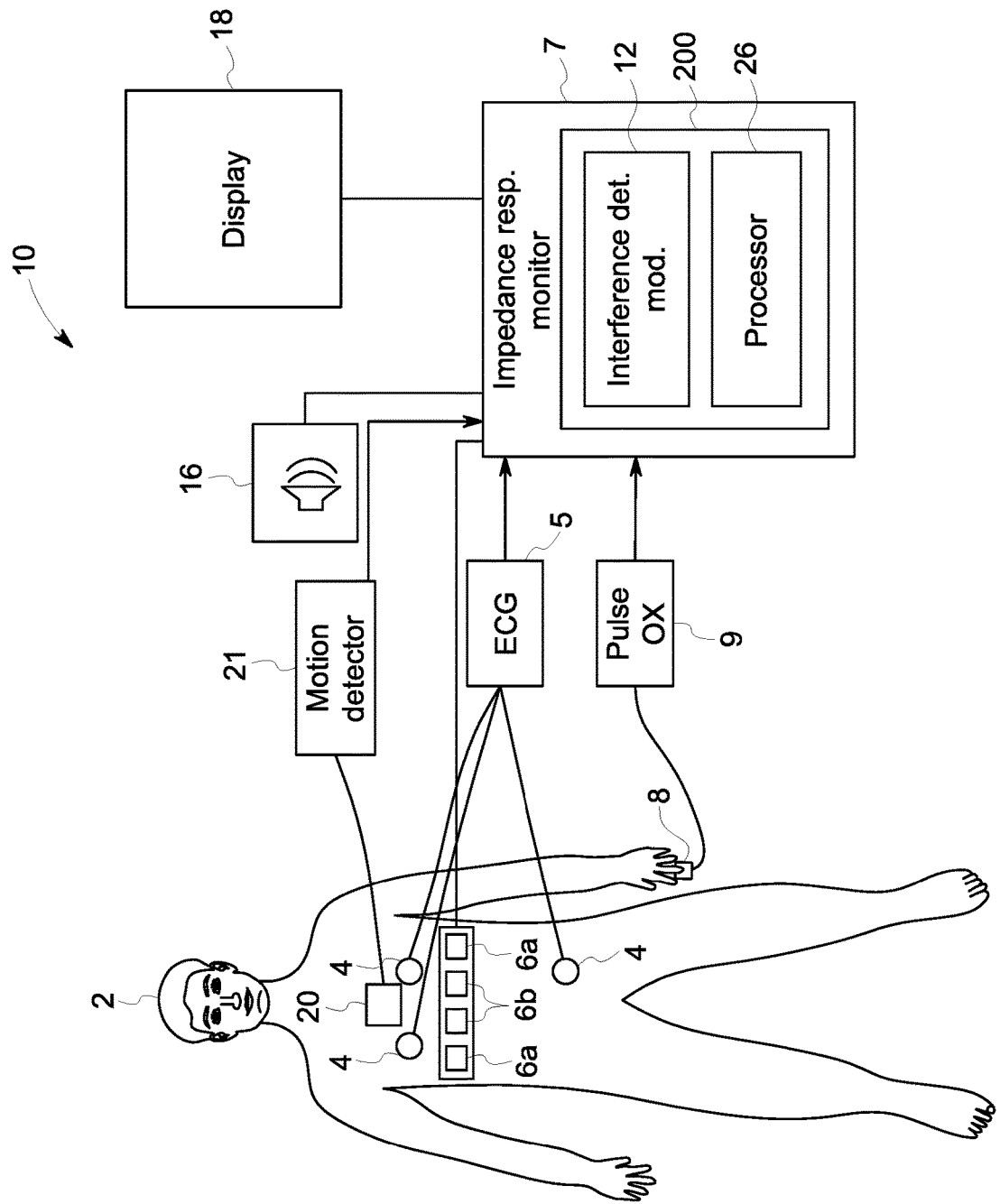
FIG. 1 is a schematic diagram of one embodiment of patient monitoring system having an impedance respiration monitor and an interference detection module.

The inventor has recognized that prior art methods and systems for addressing interference by patient monitors with minute ventilation rate-adaptive pacemakers (MV controlled pacemakers) have been insufficient. Previous solutions include educating doctors and patients regarding the interference issue, avoiding use of impedance monitors for patients with MV controlled pacemakers, and/or reprogramming MV controlled pacemakers to a non-rate-adaptive passing mode when impedance monitors are used. Further, certain currently-available patient monitors provide a warning to clinicians upon start up reminding them of the possible interference issues and to check whether the patient has an MV controlled pacemaker.

The present inventor has recognized that prior art solutions do not sufficiently address the problem of interference with MV controlled pacemakers, and that pacemaker tachycardia due to interference from patient monitors continues to pose a risk. The inventor has also recognized that it is practically impossible for a patient monitor to directly detect the presence of an MV controlled pacemaker because the bio-impedance measurement by the pacemaker is very local and the impedance measurement currents are too small to be reliably measured from the patient's skin.

The inventor has further recognized that clinicians treating a patient may not always be aware of the fact that a patient has a pacemaker, let alone be informed of the type of pacemaker implanted in a patient. While some currently-available patient monitoring devices do include pacemaker detection features that detect the presence of a pacemaker, such as a dedicated pacemaker detector in the analog front end of an ECG monitor, such detectors only provide information about the presence of a pacemaker and are generally unable to identify the type of pacemaker implanted in a patient. Thus, such pacemaker detectors cannot provide information about the presence of an MV controlled pacemaker. Moreover, the pacemaker detector may fail to detect a pacemaker, or certain monitoring devices may not be equipped with such pacemaker detectors. Thus, a clinician may be unable to detect whether a patient has a pacemaker. Moreover, clinicians may not have access to a patient's medical record in order to know about the patient's pacemaker, especially in emergency care situations or situations where the patient's medical record is incomplete or inaccessible. In such situations, clinicians need assistance in order to detect interference by patient monitors with a patient's pacemaker and/or to prevent such monitoring from significantly changing the heart rate dictated by the pacemaker.

Upon recognition of the short comings of the presently available solutions to the long standing problem of interference with MV controlled pacemakers by patient monitors using impedance measurements, the inventor developed the disclosed solution whereby a baseline heart rate is calculated prior to any impedance measurements by the patient monitor, such as an impedance respiration monitor, and then the heart rate is monitored for an interference check period after activation of the impedance measurements by the patient monitor to determine whether a significant change occurs in the heart rate indicator for the patient compared to the baseline heart rate. If the heart rate indicator changes by the threshold amount, an interference alert is generated prompting the clinician to assess whether the impedance measurement is interfering with a pacemaker on the patient. Additionally, the impedance measurements by the patient monitor may be automatically deactivated, or stopped, upon detection of the threshold change in the heart rate indicator during the interference check period.

Moreover, after the interference check period and during continued impedance measurement by the patient monitor, the system may continue assessing the heart rate indicator to determine whether it exceeds a high threshold, which is a threshold well-above a normal resting heart rate for a patient. If the heart rate indicator exceeds the high threshold while the patient monitor is conducting impedance measurements, the system may generate a possible interference warning prompting a clinician to assess whether the impedance measurement is interfering with the pacemaker. In certain embodiments, the system may assess whether the patient is undergoing physical activity that may naturally cause the high heart rate. For instance, the system may include a motion detection unit to measure the patient motion and determine whether substantial patient motion is occurring that is associated with an increased heart rate, such as the patient walking or otherwise undergoing strenuous motion. If substantial patient motion is detected, then the possible interference warning may be suppressed. If the patient monitoring device includes an ECG front end equipped with a highly reliable pacemaker detector, the interference warning may be suppressed when the presence of a pacemaker has not been detected. Also, the interference warning may be suppressed if the tachycardic rhythm has so much variability that it is considered to originate from a spontaneously beating heart rather than a pacemaker.

FIG. 1 provides a schematic diagram of an exemplary patient monitoring system 10 having an impedance respiration monitor 7 and an interference detection module 12 associated therewith to detect possible interference with a pacemaker on the patient 2. In various embodiments, the impedance respiration monitor 7 may be an impedance pneumograph, an impedance spirograph, an impedance plethysmograph, an impedance based apnea monitor, or similar. The exemplary patient monitoring system 10 further includes an electrocardiograph (ECG monitor) 5 and a pulse oximeter 9. Both the ECG monitor 5 and the pulse oximeter 9 can provide a heart rate indicator based on physiological parameters measured from the patient. The ECG monitor 5 has ECG electrodes 4 that sense cardiac potentials from the patient 2, based upon which the ECG monitor 5 determines a heart rate. The pulse oximeter 9 includes a sensor 8 that senses an arterial pulse, based upon which the pulse oximeter determines a pulse rate. Both the heart rate provided by the ECG monitor 5 and the pulse rate provided by the pulse oximeter 9 are heart rate indicators that may be utilized by the interference detection module 12 in order to detect interference with a pacemaker on the patient 2 and/or as a means for assessing the pacemaker function and for controlling the impedance measurements from the impedance respiration monitor 7 accordingly. In certain embodiments, the patient monitoring system 10 may include only one patient monitor capable of providing a heart rate indicator, such as either the ECG monitor 5 or the pulse oximeter 9, or some other patient monitor capable of providing a heart rate indicator.

In the depicted embodiment, the impedance respiration monitor 7 is associated with a set of four electrodes for measuring impedance across a patient's chest to provide a respiration rate. Specifically, the impedance respiration monitor 7 measures changes in impedance of the patient's chest caused by expansion and contraction of the patient's chest during respiration in order to provide the respiration rate or detect apnea, i.e. cessation of breathing. One possible electrode arrangement for this purpose is depicted, which includes two drive electrodes 6*a* to inject an AC current into the tissue of the patient's chest. The AC current causes a potential difference to develop across any two points between the drive electrodes. This potential difference is reflected in the resistivity of the tissue between two voltage-sensing, or receiving electrodes 6*b*. The impedance is then determined based on the voltage difference between the two receiving electrodes 6*b* and the current that flows through the tissue. The depicted electrode arrangement is merely exemplary, and multiple other electrode arrangements are known. In certain embodiments, the impedance respiration monitor 7 may employ a two terminal, or two electrode, measurement technique. In other embodiments, three electrodes may be employed. In still other embodiments, more than four electrodes may be utilized. In still other embodiments, the impedance measurements may be conducted by the same electrodes as used for monitoring the cardiac potentials. In such embodiments, the ECG electrodes 4 and the respiration electrodes 6 may be combined into one set of three or more electrodes which may serve dual purposes of monitoring respiration rate and cardiac potentials. In such embodiments, the ECG monitor 5 and the respiration monitor 7 are incorporated into the same, multi-parameter monitoring device. The same multi-parameter monitoring device may further include a circuit mechanism to detect voltage pulses generated by the pacemaker. The information from the detector is used for indicating the time points of pacing on top of the electrocardiogram. Regularly detected pulses indicate a presence of a pacemaker, which information can be used for modifying how the user is notified about the possible heart rate change.

In certain embodiments, the system 10 may further include a motion detector 21 that detects patient motion by any of various means and produces motion data indicating patient motion. In such embodiments, the interference detection module 12 receives the motion data from the motion detector 21 and determines whether substantial patient motion is occurring that would indicate or be associated with an increased heart rate for the patient. Accordingly, if the patient's heart rate does increase, the interference detection module can determine whether such interference is likely due to the patient's activity and increased respiration rate, or likely due to an interference caused by the impedance measurements conducted by the impedance respiration monitor 7. In certain embodiments, the motion detector 21 may be part of a motion detection unit that includes one or more accelerometers 20 fastened or otherwise connected to the patient 2 to measure the patient's motion and or position. For example, one or more accelerometers 20 may be attached at various points in the patient, such as the patient's chest, torso, arms, legs, etc. to measure the local motion of the patient, and such information may be aggregated to provide motion data, which is information about the patient's activity. For example, the accelerometer 20 may be a three-access accelerometer, in other embodiments, the patient's motion may be measured by a combined gyroscope-accelerometer, which allows movement and orientation tracking. In still other embodiments, the motion detector unit may utilize a sensor cable of acting as an accelerometer and/or gyroscope.

In such an embodiment, the accelerometer 20 (or like sensor) provides motion data 34 (see FIG. 2), which the motion detector 21 and/or interference detection module 12 use to determine whether substantial patient motion is occurring that would indicate that an elevation in the patient's heart rate is proper and justified based on the patient's activity level. For example, the motion detector 21 may analyze the acceleration measurements from each of the one of more accelerometers 20 on the patient 2 and may classify that information into motion data describing the patient's activity or activity level—e.g., indicating whether the patient is sitting, standing, walking, etc., or indicating a level of strenuousness of the patient motion—based on the magnitude and direction of acceleration measurements and/or patterns therein. If substantial patient motion is occurring that is associated with an increased heart rate, such as the patient walking or otherwise engaging in activity that meets a predetermined threshold level of strenuousness, then the substantial patient motion is determined to explain the increased heart rate. In certain embodiments, the threshold of determining substantial patient motion is based on the heart rate indicator, where more strenuous activity levels are required to justify higher heart rates.

In still other embodiments, the motion detection unit may not employ any sensor associated with the patient, and the motion detector 21 may measure patient motion by other means. For example, the motion detector 21 may assess a signal quality index of one or more of the physiological signals measured from the patient, such as by the ECG monitor 5 and/or the pulse oximeter 9, to provide motion data regarding the patient's motion and/or activity level. For example, the motion detector 21 may be configured to assess the signal quality index of each patient monitor associated with the patient 2, and to recognize certain noise features or signal quality features which may be specific to that particular monitoring device and are indicative of the fact that the patient is engaged in significant activity. The motion detector 21 may also look for patterns or correlations between the monitoring devices that might indicate particular types of patient motion, and may provide such information in motion data 34 supplied to the computing system 200 containing the interference detection module 12.

The computing system 200 containing the interference detection module 12 is associated with the respiration monitor 7 and, in some embodiments, is capable of controlling function of the impedance respiration monitor 7. In the depicted embodiment, the computing system 200 is housed within the impedance respiration monitor 7. In other embodiments, the computing system 200 may be a separate control system, such as in a central hub associated with impedance respiration monitor 7 in an arrangement such that control signals can be sent from the computing system 200 to the impedance respiration monitor 7 in order to control the function thereof. In the depicted embodiment, the impedance respiration monitor 7 receives the ECG heart rate 30 from the ECG monitor 5 and the pulse rate 32 from the pulse oximeter 9, as well as motion data 34 from the motion detector 21 and a respiration rate 36 from the impedance respiration monitor 7. In embodiments where the computing system 200 is provided in a separate device from the impedance respiration monitor 7, such as in a central hub, the ECG heart rate 30, pulse rate 32, and motion data 34 may instead by supplied to such a hub device or other device containing the computing system 200. In still other embodiments, the patient monitoring system 10 may comprise a multi-parameter patient monitor encompassing the impedance respiration monitor 7 in conjunction with one or more of the ECG monitor 5, the pulse oximeter 9, or the motion detector 21. In embodiments where one or more of the various monitoring devices 5, 7, 9, 21 are separate devices they may communicate by any wired or wireless means.

The depicted embodiment shows representative connections between the various sensors on the patient 2, the patient monitor, and the computing system 200, which may be wired connections. Alternatively, various separate wireless monitoring devices, such as a wireless ECG monitor 5, a wireless pulse oximeter 9, a wireless impedance respiration monitor 7, and a wireless motion detector 21 may communicate with a hub device containing the computing system 200 having control and communication software for communicating with the various patient monitors, where the hub device includes the interference detection module 12. In such an embodiment, the various wireless patient monitors may communicate with the hub by any wireless means, including any wireless communication protocol.

The patient monitoring system 10 further includes a speaker 16 capable of enunciating alarms, alerts, warnings, etc. such as to alert a clinician regarding a possible or detected interference, and/or to prompt a clinician to assess whether the impedance measurement is interfering with the pacemaker. The patient monitoring system may further include a display 18, which may be any type of display device, such as, but not limited to, a light emitting diode display (LED), a liquid crystal display (LCD), an electroluminescent display (ELD), a plasma display panel, or the like. In certain embodiments, the display 18 may be a touchscreen display configured to receive control inputs or other input values for one or more of the various patient monitors 5, 7, 9, 21. The speaker 16 and display 18 are communicatively connected to the computing system 200 such that interference alerts 39 and/or possible interference warnings 40 may be auditorily and visually provided to a clinician. Such communicative connections may be by any wired or wireless means, and may be direct or indirect control. For example, the speaker 16 and/or display 18 may be incorporated locally into one of the monitoring devices 5, 7, 9, 21, or into a central hub device located in the vicinity of the patient 2. Alternatively or additionally, one or more speakers 16 and displays 18 may be communicatively connected to the computing system 200 via the computer network of the healthcare facility, and such speakers 16 and displays 18 may be provided at various locations other than at the patient's bedside, such as at a central nurses station and/or at mobile units carried by clinicians. A patient monitor may have a mechanism to alarm based on detection of a heart rate that exceeds an alarm threshold. The source of the heart rate may be ECG monitor or pulse oximeter, for example. When a high heart rate alarm is annunciated, the monitor may simultaneously display a notification that the high heart rate may be originating from a pacemaker device experiencing interference from the monitor's impedance measurement. In certain embodiments, this warning is may be made conditional on the presence of pacemaker pulses detected by the monitor. Alternatively, the monitor may count the frequency of detected pacemaker pulses as a surrogate for the actual heart rate.

Figure 2:
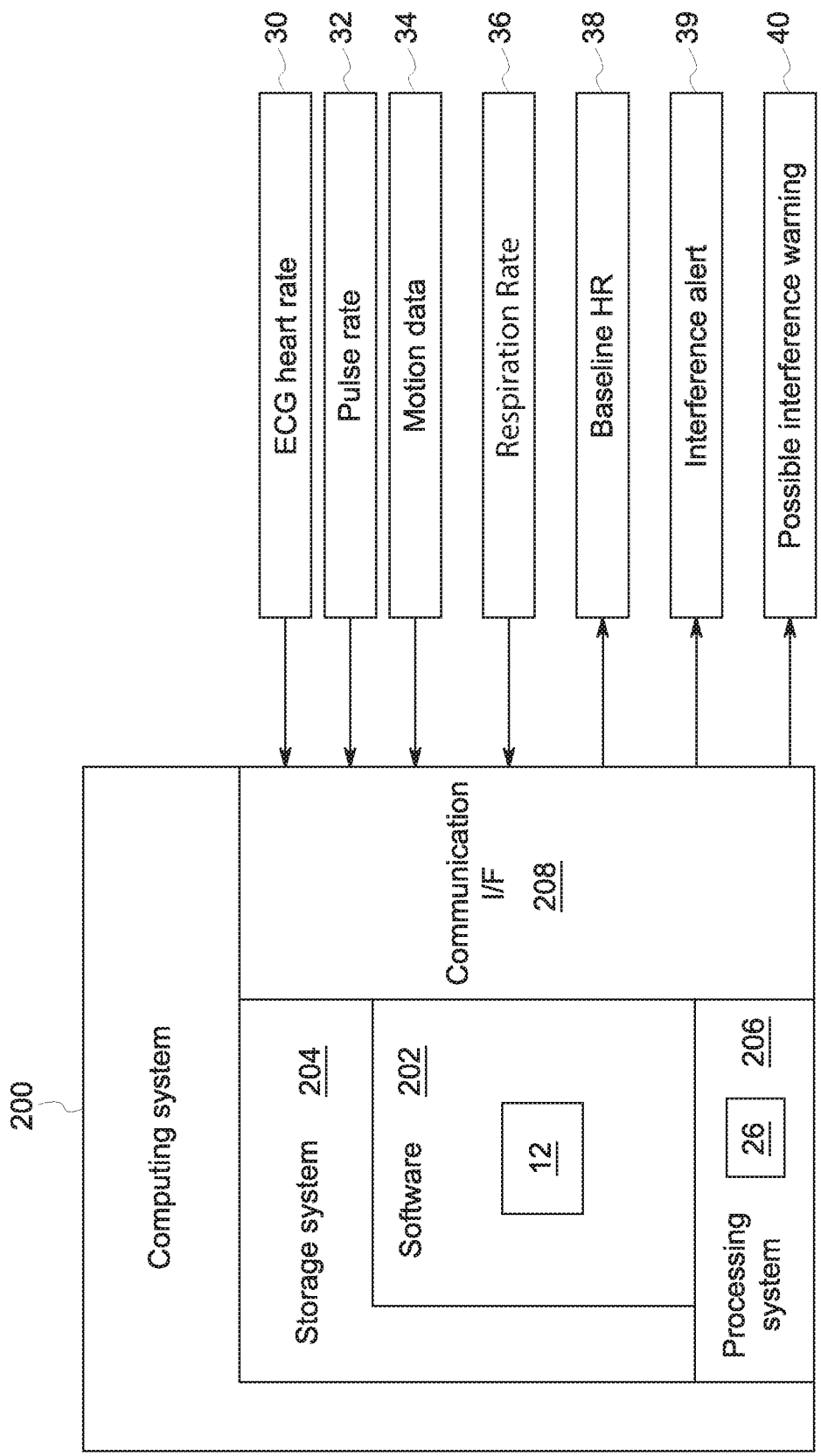
FIG. 2 is a schematic diagram of an exemplary computing system incorporated in or associated with the patient monitoring system.

FIG. 2 provides a system diagram of an exemplary embodiment of the computing system 200 having an interference detection module 12 executable to provide the pacemaker interference detection and control functions described herein. The computing system 200 generally includes a processing system 206, storage system 204, software 202, and a communication interface 208. The processing system 206 loads and executes software 202 from the storage system 204, including the interference detection module 12, which is an application within the software 202. The interference detection module 12 includes computer-readable instructions that, when executed by the processing system 206, direct the patient monitoring device 10 to operate as described in the various embodiments disclosed herein.

Although the computing system 200 as depicted in FIG. 2 includes one software 202 encapsulating one interference detection module 12, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 26, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the one or more speakers 16, display 18, and the various patient monitors 5, 7, 9, 21, and/or any dedicated control system associated therewith, in order to receive the data inputs and provide control outputs described herein. Thus, the communication interface facilitates receipt of the ECG heart rate 30, pulse rate 32, motion data 34, and respiration rate 36 from the respect patient monitors 5, 7, 9, 21 for use by the interference detection module 12. The interference detection module 12 contains computer readable instructions that, when executed on the processor 26, carry out the method steps described herein, including to determine the baseline heart rate 38, detect possible interference with a pacemaker on the patient, and generate an interference alert 39 and/or possible interference warning 40, as appropriate. For example, the computing system 200 may control one or more speakers 16 and/or displays 18 to generate auditory and/or visual alerts/warnings.

Figure 3:
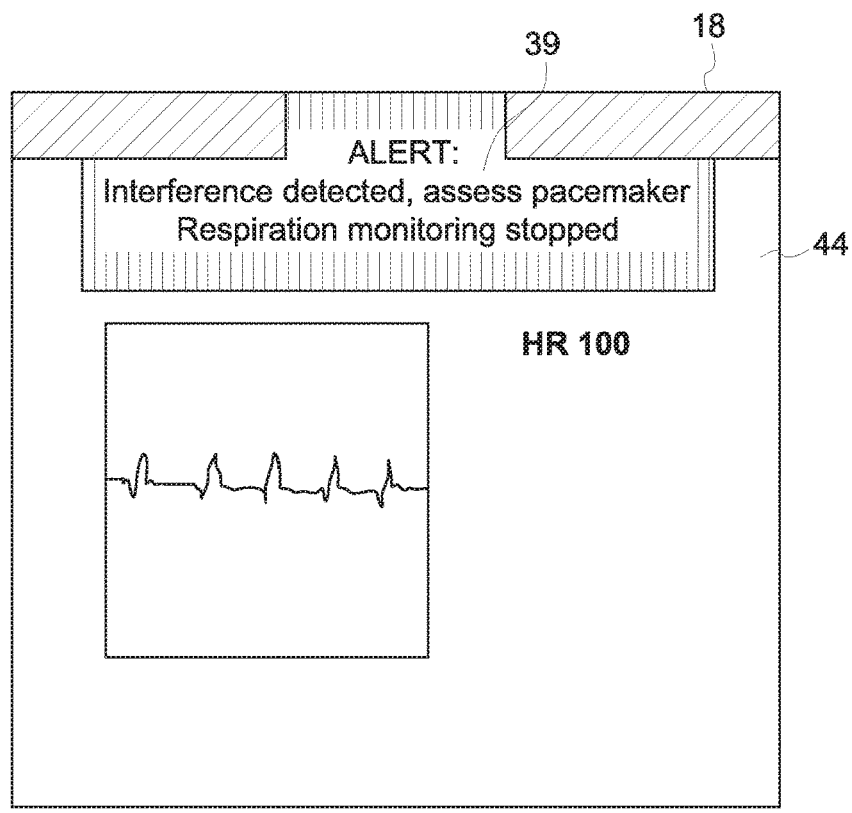
FIG. 3 depicts an exemplary display screen associated with the patient monitoring system providing an exemplary interference alert.

FIG. 3 depicts one embodiment of a display screen 44 providing an exemplary interference alert 39 generated upon detecting a threshold change in the heart rate indicator (e.g. in the ECG heart rate 30 and/or the pulse rate 32) during an interference check upon activating the respiration monitor 7 to conduct impedance measurements. In the depicted embodiment, the interference 39 includes a visual alert provided on a display screen 44 of the display 18. The visual interference alert 39 provides notification to a clinician regarding the detected interference with the pacemaker on the patient 2, and may prompt the clinician to assess the patient's condition and/or the function of the pacemaker. Moreover, in embodiments where the interference detection module 12 is further executable to automatically deactivate the impedance respiration monitor 7 upon detection of a threshold change in the heart rate indicator 30, 32 during the interference check period, the interference alert 39 may further advise a clinician that the respiration monitoring by the impedance respiration monitor 7 has stopped due to the detected interference.

Figure 4:
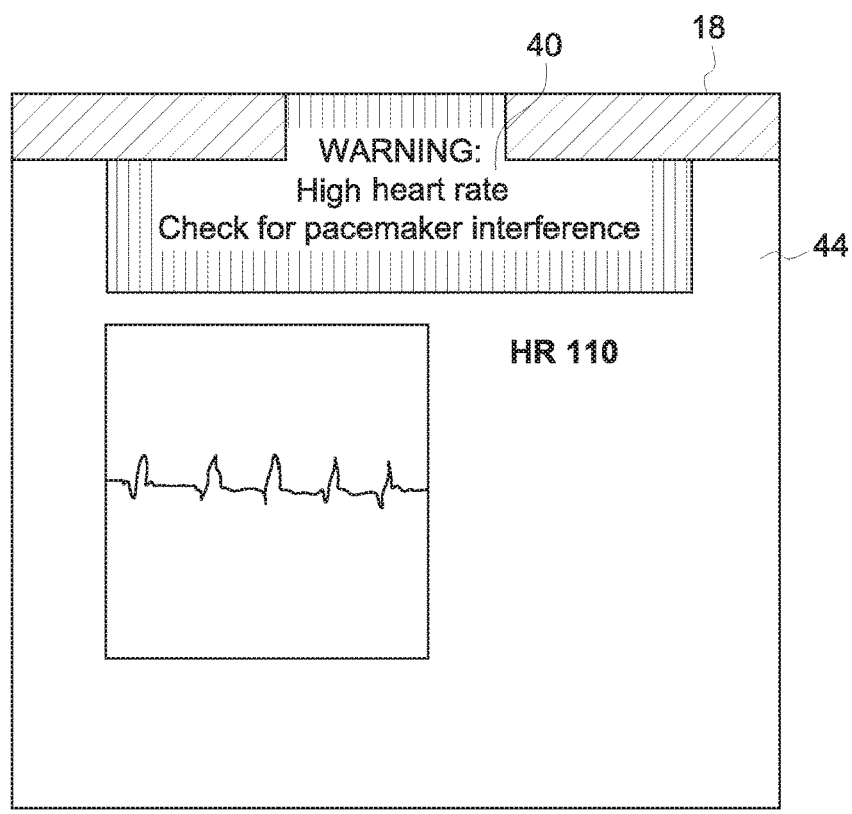
FIG. 4 depicts an exemplary display screen of a patient monitoring system depicting an exemplary possible interference warning.

FIG. 4 depicts a display screen 44 on the display 18 providing an exemplary possible interference warning 40 generated upon detecting that the heart rate indicator 30, 32 has exceeded a high threshold during operation of the impedance respiration monitor 7 to monitor patient respiration (but after the interference check period). The possible interference warning 40 advised the clinician that a high heart rate is detected and prompts the clinician to access whether the impedance measurement is interfering with the pacemaker. As will be understood by a person having ordinary skill in the art, the interference alert 39 and the possible interference warning 40 may be displayed in any number of ways, and the figures are intended only to exemplify one possible display and exemplary display content. Moreover, it should be understood that the interference alert 39 and the possible interference warning 40 may also include an auditory component, or may be provided only as an auditory alert/warning with no visual component.

Figure 5:
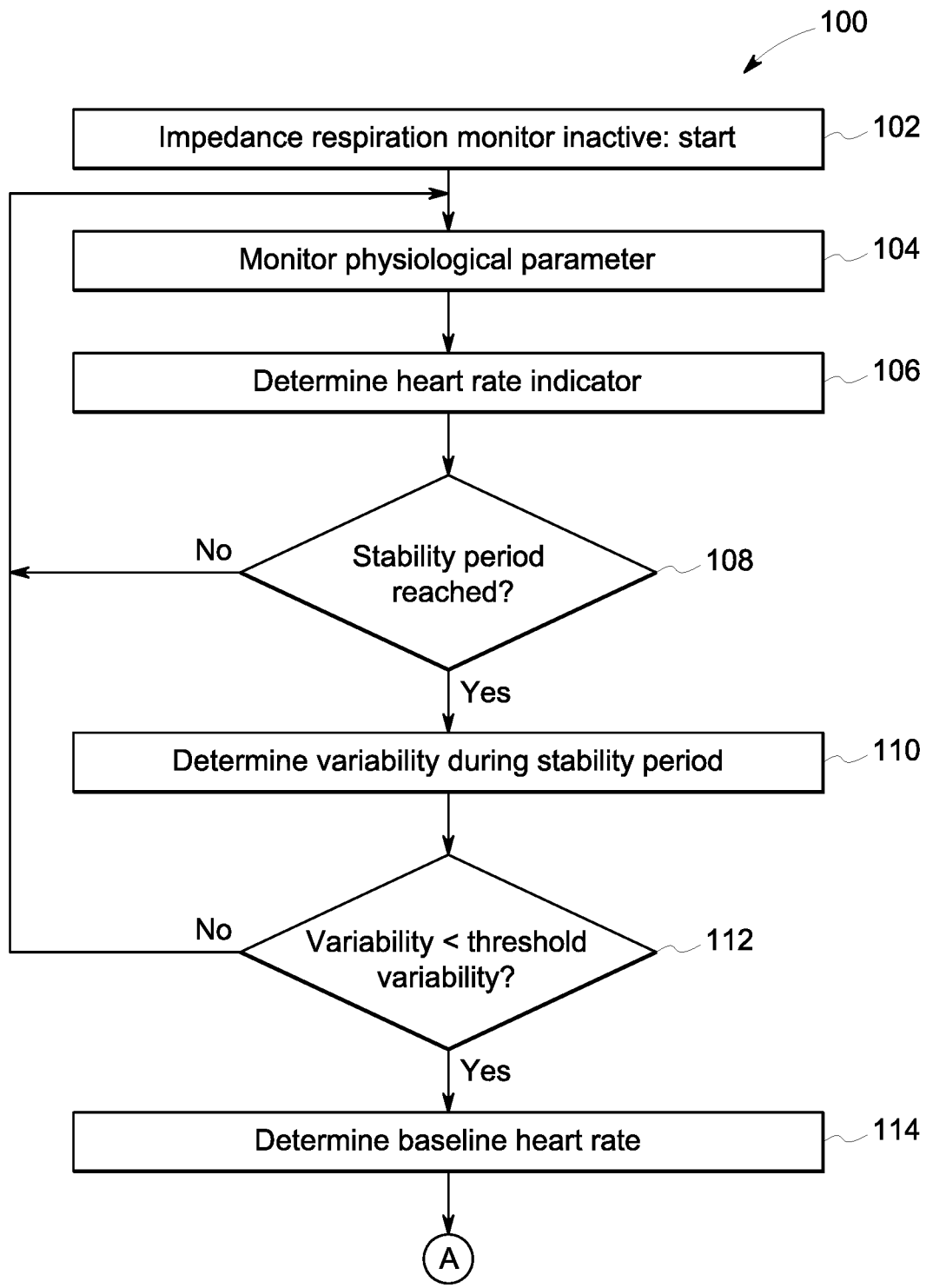
FIGS. 5-7 depict exemplary methods, or portions thereof, of controlling an impedance respiration monitor in accordance with the present disclosure.
Figure 6:
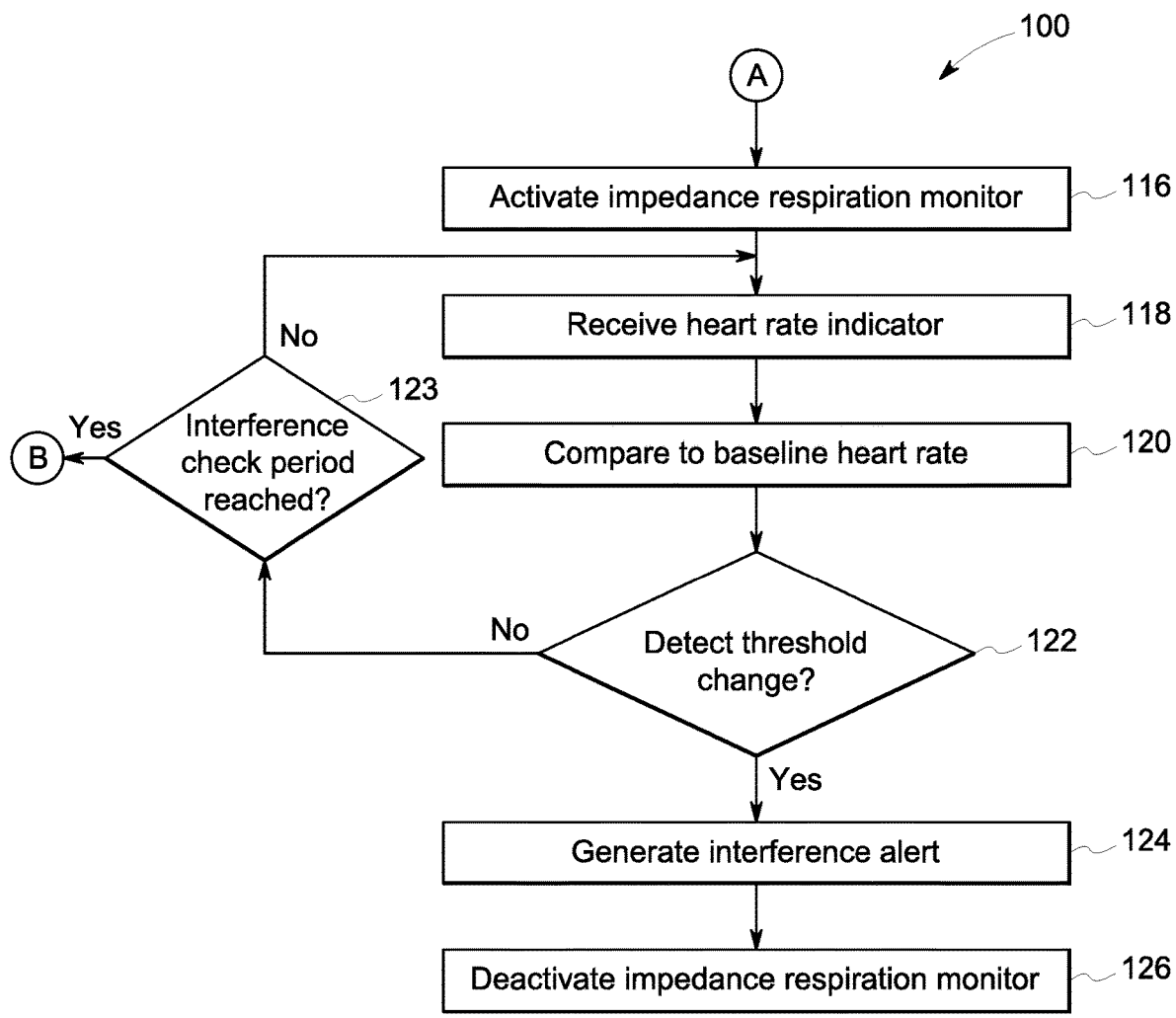
Figure 7:
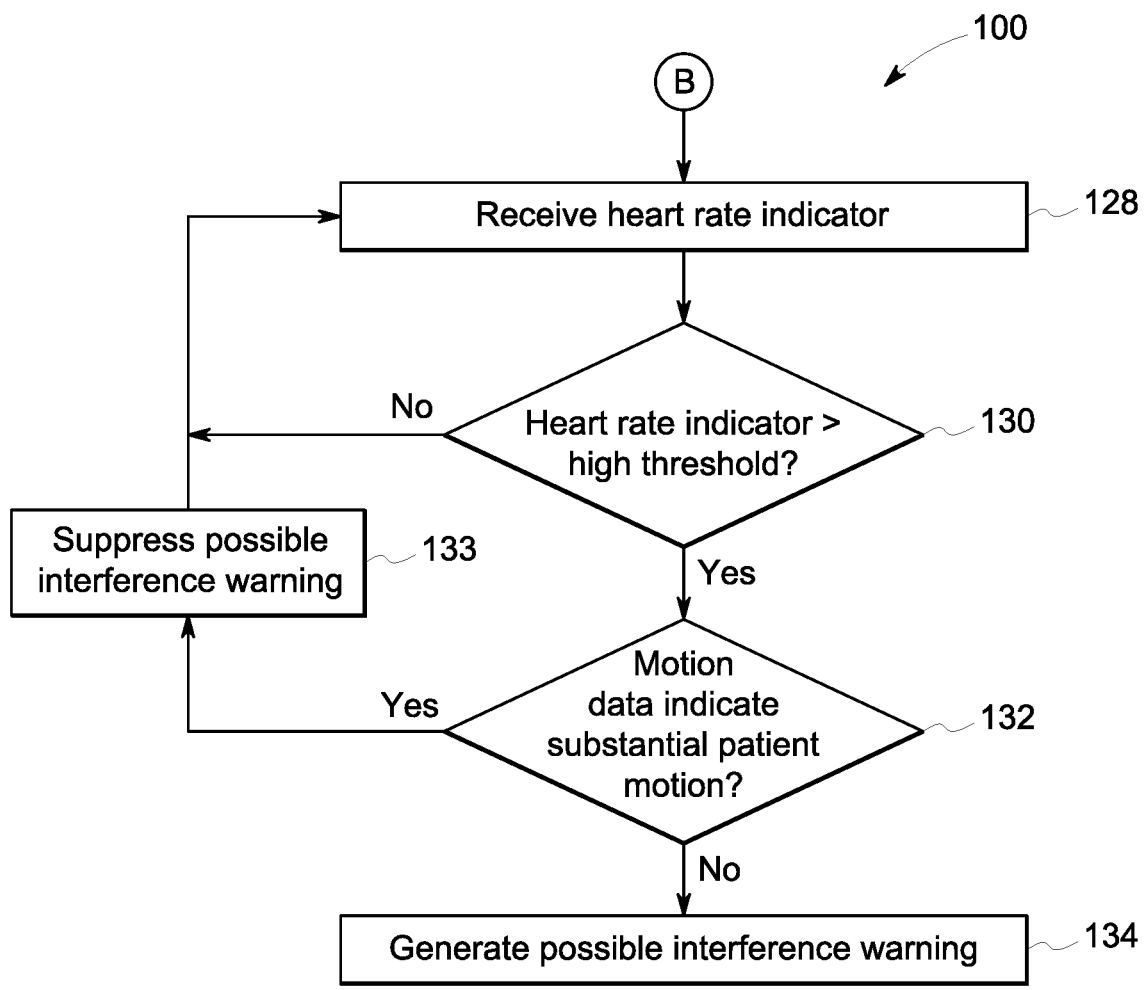

FIGS. 5-7 provide exemplary embodiments of methods 100 of controlling impedance measurement by a patient monitor, such as controlling an impedance respiration monitor 7 to monitor respiration of a patient 2. The method 100 begins at step 102 with the impedance respiration monitor 7 inactive—i.e. not conducting impedance measurements of the patient's chest. The physiological parameter from which the heart rate indicator is calculated is monitored at step 104 and the heart rate indicator is determined at step 106. For example, the physiological parameter may be cardiac potentials measured by the ECG monitor 5, based on which the ECG heart rate 30 is calculated. In other example, the heart rate monitor includes a pulse oximeter 9, wherein the physiological parameter is an arterial pulse of the patient and the heart rate indicator is a pulse rate 32 for the patient. In other embodiments, the heart rate indicator may be provided by other values that are indicative of heart rate. Steps 104 and 106 are repeated for the stability period, and thus the heart rate indicator is tracked for the stability period. Once the stability period is reached at step 108, a variability of the heart rate indicator is determined for the stability period at step 110. The variability for the heart rate indicator is compared to a threshold variability indicating that the heart rate is stable and that the heart rate indicator is a sufficiently accurate indicator of heart rate (e.g., that the heart rate indicator is not unreliable due to excess noise or other artifact, a malfunctioning sensor, etc.). If the variability of the heart rate indicator is too high, then the method continues to monitor the physiological parameter and calculate the heart rate indicator until the heart rate indicator meets the threshold variability requirement for the stability period.

To provide just one example, the stability period may be in the range of 30 seconds to a few minutes, and may vary based on the monitoring context (such as the type and inherent variability of the heart rate indicator being used (or the physiological parameter on which the heart rate indicator is based), whether the patient has an underlying condition that may cause variation in heart rate, whether the physiological parameter is being measured in a noisy environment, etc.). In certain examples, the threshold variability for the heart rate indicator could be a value in the range of two to five beats per minute, which again may be an adjustable value to accommodate the realities of certain monitoring environments and certain patient physiologies.

Once the threshold variability requirement is met, the baseline heart rate is determined at step 114. For example, the baseline heart rate may be one heart rate indicator value calculated based on physiological parameters measured during the predefined stability period. In one example, the baseline heart rate 38 may be the last execution of step 106 during the stability period (assuming that the threshold stability is not exceeded at step 112). Alternatively, the baseline heart rate may be an average or a mean of the heart rate indicators calculated during the stability period. In still other embodiments, the threshold variability analysis may be eliminated, and the baseline heart rate 38 may be determined as a calculation, such as the average or mean of the heart rate indicators over the stability period (without any variability check).

Once the baseline heart rate is determined, the interference detection module 12 executes steps to activate the impedance measurements by the impedance respiration monitor 7 and assess whether pacemaker interference is detected. FIG. 6 provides an exemplary embodiment of such steps. In the depicted example, the impedance respiration monitor 7 is activated at step 116, and then the heart rate indicator is assessed for an interference to determine whether interference is occurring. In the depicted embodiment, the heart rate indicator is received at step 118 and compared to the baseline heart rate at step 120. If a threshold change in the heart rate indicator is detected at step 122, which is based on the comparison conducted at step 120, then an interference alert is generated at step 124. Exemplary interference alerts 39 are described herein, which may include visual and/or auditory components that notify a clinician regarding interference with a pacemaker on the patient. The impedance respiration monitor is deactivated at step 126 to stop the impedance measurement on the patient's chest, and thereby to stop the activity that is interfering with the pacing by the pacemaker. The heart rate indicator is monitored for the interference check period, and if the interference check period is reached at step 123 without detection of the threshold change, then the initial interference check is complete and the impedance respiration monitoring continues respiration monitoring as usual.

In one example, the threshold change in the heart rate indicator is a predefined value between 20 beats per minute and 30 beats per minute, and the interference check period is a predefined period between two minutes and ten minutes. In other examples, the threshold change and interference check period values may differ from, or be outside of, those ranges.

In certain embodiments, the interference detection module 12 may continue to monitor the heart rate indicator during impedance measurements by the impedance respiration monitor 7 to detect whether a possible interference develops after the interference check period. FIG. 7 exemplifies one embodiment of such steps. As each heart rate indicator is received at step 128, the heart rate indicator is compared to a high threshold at step 130. To provide just one example, the high threshold may be a predefined value between 110 beats per minute and 120 beats per minute, which is generally considered a very high heart beat and is approaching an upper maximum for many pacemakers, which is often in the range of 120 to 130 beats per minute. In certain embodiments, the high threshold may be an adjustable value that can be set by a clinician based on the patient's condition and the expected activity of a patient during the monitoring period. In certain embodiments the threshold can be the same as a 'high heart rate' alarm threshold in a patient monitor. In certain embodiments, the heart rate indicator received at step 128 may be a filtered value in order to avoid reacting to transient changes in the heart rate indicator, such as resulting from transient erroneous measurements due to noise.

In certain embodiments, a possible interference warning 40 may be generated after the high threshold is exceeded. In the example of FIG. 7, once the heart rate indicator is determined at step 130 to be above the high threshold, then the interference detection module 12 executes instructions to access information about the patient's motion to see if the increase in the heart rate indicator is due to physiological changes in the patient, such as due to an increase in the patient's activity level. Motion data is assessed at step 132, which is received from the motion detector 21, to determine whether the motion data indicates substantial patient motion associated with an increased heart rate. If substantial patient motion is detected, then the possible interference warning may be suppressed at step 133. If substantial patient motion is not detected, then a possible interference warning is generated at step 134 to prompt a clinician to assess whether the impedance measurement is interfering with a pacemaker on the patient. Exemplary possible interference warnings 40 are exemplified and described herein, which may include visual and/or auditory components. The possible interference warning is intended to remind clinicians to assess whether the tachycardia may be due to interference with a possible pacemaker on the patient before diagnosing and treating a patient for an emergency heart condition, such as ventricular tachycardia.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A patient monitoring system comprising:
 a heart rate monitor configured to measure a physiological parameter from a patient and provide a heart rate indicator based on the physiological parameter;
 an impedance respiration monitor configured to measure impedance of the patient's chest and provide a respiration rate;
 a processor;
 an interference detection module executable on the processor to:
  while the impedance respiration monitor is not active, receive the heart rate indicator from the heart rate monitor;
  determine baseline heart rate;
  activate the impedance respiration monitor to measure impedance of the patient's chest to provide the respiration rate;
  upon activating the impedance respiration monitor, assess the heart rate indicator for an interference check period;
  detect a threshold change in the heart rate indicator during the interference check period compared to the baseline heart rate indicating that the impedance respiration measurement has interfered with a pacemaker on the patient; and
  generate an interference alert to notify a clinician regarding interference with the pacemaker on the patient.

2. The patient monitoring system of claim 1, wherein the interference detection module is further executable to automatically deactivate the impedance respiration monitor upon detection of the threshold change in the heart rate indicator during the interference check period.

3. The patient monitoring system of claim 1, wherein the threshold change in the heart rate indicator is a predefined value between 20 beats per minute and 30 beats per minute.

4. The patient monitoring system of claim 1, wherein the interference check period is a predefined period between 2 and 10 minutes.

5. The patient monitoring system of claim 1, wherein the baseline heart rate is determined based on the heart rate indicator for a predefined stability period.

6. The patient monitoring system of claim 5, wherein the interference detection module is further executable to determine that a variability of the heart rate indicator is less than a threshold variability during the predefined stability period prior to determining the baseline heart rate, and wherein the baseline heart rate is a heart rate indicator based on one or more physiological parameter measurements during the predefined stability period.

7. The patient monitoring system of claim 1, wherein the interference detection module is further executable to:
 assess the heart rate indicator while the impedance respiration monitor is active;
 detect that the heart rate indicator exceeds a high threshold; and
 generate a possible interference warning prompting a clinician to assess whether the impedance measurement is interfering with the pacemaker.

8. The patient monitoring system of claim 7, wherein the high threshold is a user-adjustable alarm threshold for high heart rate.

9. The patient monitoring system of claim 1, further including a motion detection unit configured to measure patient motion and produce motion data, and wherein the interference detection module is further executable to suppress the possible interference warning when the motion data indicates substantial patient motion associated with increased heart rate.

10. The patient monitoring system of claim 9, wherein the motion detection unit includes one or more accelerometers measuring the patient motion.

11. The patient monitoring system of claim 1, wherein the heart rate monitor includes an electrocardiograph, wherein the physiological parameter is cardiac potentials.

12. The patient monitoring system of claim 1, wherein the heart rate monitor includes a pulse oximeter, wherein the physiological parameter is arterial pulse and the heart rate indicator is pulse rate.

13. The patient monitoring system of claim 1, wherein the impedance respiration monitor includes an impedance pneumograph.

14. A method of controlling an impedance respiration monitor to monitor respiration of a patient, the method comprising:
 receiving a heart rate indicator from a heart rate monitor for at least a predefined stability period when the impedance respiration monitor is not active to measure impedance of the patient's chest;
 determine a baseline heart rate for the patient based on the heart rate indicator during the predefined stability period;
 activating the impedance respiration monitor to measure impedance of the patient's chest and provide a respiration rate;
 upon activating the impedance respiration monitor, assessing the heart rate indicator for an interference check period, including:
  comparing the heart rate indicator to the baseline heart rate;
  detecting a threshold change in the heart rate indicator during the interference check period indicating that the impedance respiration measurement has interfered with a pacemaker on the patient;

generating an interference alert to notify a clinician regarding interference with a pacemaker on the patient.

15. The method of claim 14, further comprising automatically deactivating the impedance respiration monitor upon detection of the threshold change in the heart rate indicator during the interference check period.

16. The method of claim 14, wherein the threshold change in the heart rate indicator is a predefined value between 20 beats per minute and 30 beats per minute, and wherein the interference check period is a predefined period between 2 and 10 minutes.

17. The method of claim 14, further comprising determining that a variability of the heart rate indicator is less than a threshold variability during the predefined stability period prior to determining the baseline heart rate.

18. The method of claim 14, further comprising continuing to assess the heart rate indicator while the impedance respiration monitor is active;

detecting that the heart rate indicator exceeds a high threshold; and generating a possible interference warning prompting a clinician to assess whether the impedance measurement is interfering with the pacemaker.

19. The method of claim 14, further comprising:

detecting substantial patient motion associated with increased heart rate; and suppressing the possible interference warning while the substantial patient motion is detected.

20. The method of claim 19, wherein detecting patient motion includes receiving input from one or more accelerometers measuring patient motion.

* * * * *